US010111989B2

(12) United States Patent
Foley et al.

(10) Patent No.: US 10,111,989 B2
(45) Date of Patent: Oct. 30, 2018

(54) SPLASH-RETARDING FLUID COLLECTION SYSTEM

(75) Inventors: Brian Foley, Port Barrington, IL (US); XingQuan Ren, Skokie, IL (US)

(73) Assignee: Medline Industries, Inc., Northfield, IL (US)

(*) Notice: Subject to any disclaimer, the term of this patent is extended or adjusted under 35 U.S.C. 154(b) by 1432 days.

(21) Appl. No.: 13/559,285

(22) Filed: Jul. 26, 2012

(65) Prior Publication Data
US 2014/0027006 A1 Jan. 30, 2014

(51) Int. Cl.
*A61M 1/00* (2006.01)
*B65D 51/24* (2006.01)
*A61G 13/10* (2006.01)

(52) U.S. Cl.
CPC .......... *A61M 1/0001* (2013.01); *B65D 51/24* (2013.01); *A61G 13/102* (2013.01); *Y10T 29/49826* (2015.01)

(58) Field of Classification Search
CPC ............... A61M 1/0001; B65D 51/24; Y10T 29/49826; A61G 13/102
USPC ................................ 141/297, 299, 331–341
See application file for complete search history.

(56) References Cited

U.S. PATENT DOCUMENTS

| | | | | |
|---|---|---|---|---|
| 2,511,682 A * | 6/1950 | Allen | | 126/384.1 |
| 4,091,956 A * | 5/1978 | Vecchio | | 220/231 |
| 4,936,449 A | 6/1990 | Conard et al. | | |
| 5,024,343 A | 6/1991 | Lemelson | | |
| 5,047,271 A | 9/1991 | Feddersen et al. | | |
| 5,305,911 A | 4/1994 | Aylward | | |
| 5,350,079 A | 9/1994 | Larson et al. | | |
| 5,477,897 A * | 12/1995 | Scofield | | 141/105 |
| 5,483,999 A * | 1/1996 | Lampropoulos et al. | | 141/86 |
| 5,497,892 A | 3/1996 | Takatsuki | | |
| 5,707,173 A * | 1/1998 | Cottone et al. | | 405/129.55 |
| 5,769,223 A | 6/1998 | Marsh | | |
| 5,887,739 A | 3/1999 | Prevot et al. | | |
| 5,967,778 A | 10/1999 | Riitano | | |
| 6,053,314 A * | 4/2000 | Pittman | | 206/366 |

(Continued)

FOREIGN PATENT DOCUMENTS

| | | |
|---|---|---|
| JP | 2004-067214 | 3/2004 |
| JP | 2006-123938 | 5/2006 |

(Continued)

OTHER PUBLICATIONS

Choi, Hyun G., "PCT Search Report and Written Opinion", PCT/US2013/050708; Filed Jul. 16, 2013; dated Oct. 7, 2013.

(Continued)

*Primary Examiner* — Timothy L Maust
(74) *Attorney, Agent, or Firm* — Philip H. Burrus, IV

(57) ABSTRACT

A fluid collection container (1500) includes a vessel (901) and a lid (1300). A splash retarding cover (100) can be attached to a mouth (501) of the vessel (901). The splash retarding cover (100) can include a centrally disposed suspended funnel (101), a collar (102) surrounding the funnel (101), a vessel mounting ring (109), and a plurality of sloping facets (104) circumscribing the collar (102) and sloping outwardly from an outer circumference (105) of the collar (102) and terminating at the vessel mounting ring (109). An optional cache (1904) of coagulant material can be disposed within an interior of the vessel as well.

17 Claims, 16 Drawing Sheets

(56) References Cited

U.S. PATENT DOCUMENTS

| | | | |
|---|---|---|---|
| 6,629,602 B1 | 10/2003 | Heyman | |
| 6,681,925 B2 | 1/2004 | Fischer et al. | |
| 6,719,017 B1 * | 4/2004 | McArthur et al. | 141/86 |
| D502,993 S * | 3/2005 | McArthur et al. | D24/131 |
| 7,174,928 B1 | 2/2007 | Lampropoules | |
| 7,225,927 B2 | 6/2007 | Sweeney | |
| 7,458,463 B2 | 12/2008 | Lampropoules | |
| 7,507,062 B2 | 3/2009 | Pasty | |
| 7,597,206 B2 | 10/2009 | Atkins et al. | |
| 7,644,834 B2 * | 1/2010 | Castora et al. | 220/731 |
| 7,665,491 B2 | 2/2010 | Lampropoules | |
| 7,967,147 B2 | 6/2011 | Mimura | |
| 8,127,963 B2 | 3/2012 | Gerson et al. | |
| 2007/0032764 A1 | 2/2007 | Lampropoules | |

FOREIGN PATENT DOCUMENTS

| | | |
|---|---|---|
| JP | 2009-280284 | 12/2009 |
| JP | 2011-073701 | 4/2011 |

OTHER PUBLICATIONS

Bui, Luan K., "Notice of Allowance", U.S. Appl. No. 13/283,421, filed Oct. 27, 2011; dated Sep. 4, 2014.

Bui, Luan Kim, "NonFinal OA", U.S. Appl. No. 13/283,421, filed Oct. 27, 2011; dated Feb. 7, 2014.

* cited by examiner

SPLASH-RETARDING FLUID COLLECTION SYSTEM

BACKGROUND

Technical Field

This invention relates generally to collection devices, and more particularly to fluid collection devices.

Background Art

Collection and disposal of fluids can be a complex process. While water can merely be poured down a drain, if the fluid is a toxic, hazardous, or environmentally unfriendly substance, such as a petroleum product or biological waste, care must be taken when collecting, containing, and disposing of such materials. For example, medical professionals, such as those working in a catheter or blood laboratory, must take care to properly dispose of fluids so as to avoid contaminating themselves or the environment with harmful materials.

It would be advantageous to have an improved container suitable for collection and disposal of fluids and other materials.

Figure 1:
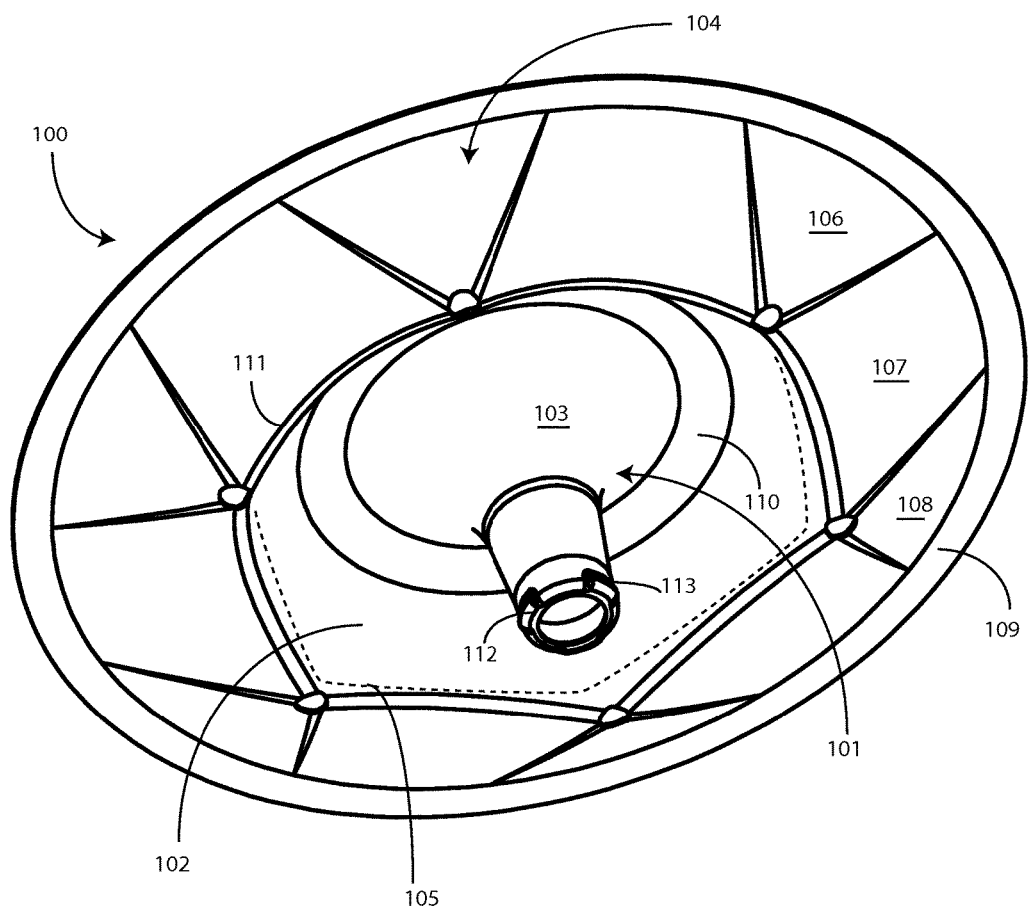
FIG. 1 illustrates a perspective view of one explanatory splash retarding cover for a containment vessel configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion.

For example, talking about a device (10) while discussing figure A would refer to an element, 10, shown in figure other than figure A. The apparatus components and method steps described below have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

Proper collection and disposal of certain fluids and other materials is an important concern. For example, in the medical space, medical professionals pay special care to the appropriate disposition of blood, urine, tissue, and other biological materials that are obtained during medical procedures. The concern of proper collection and disposal stems from a desire to avoid contamination, possible infection, and exposure to such materials, as well as to abide by applicable rules and regulations concerning the disposal of such materials.

To this end, manufacturers have developed specialized fluid collection containers. The goal of such containers is to provide a container for handling and disposing fluids, and that is also more easily accommodated storage for both fluid and particulate waste. One such fluid collection container is disclosed in U.S. Pat. No. 6,053,314 to Pittman, entitled "Receptacle for contaminated wastes."

The '314 patent attempts to provide a device configured for ready receipt and safe disposal of liquid wastes, and also to minimize the likelihood of splatter of the liquid wastes when introducing liquid into the container. The '314 patent tries to accomplish this by providing a bowl and lid. The lid includes an opening through which liquids can be poured. The opening is sealed with a sheet of adhesive film that is permanently affixed at one end, and that can be peeled from the lid on the other end. A user peels back the adhesive film while liquids are poured into the opening. The adhesive film is then pressed back across the opening to seal the container.

Such a container suffers from a number of deficiencies. As a first example, the integrity of the seal between the adhesive film and the lid is dependent upon the user. A user in a hurry may insufficiently seal the adhesive film to the lid, thereby leaving an opening through which liquids may escape the container.

A second example is more problematic. Since the adhesive film is tacky on one side and permanently affixed to the lid, a user must hold the film in a folded back position while dispensing liquids through the opening in the lid. Many users find that the folded adhesive film difficult to manage. Consequently, rather than peeling the adhesive film back, they simply remove the entire lid, thereby defeating the purpose of having a specialized container in the first place.

Embodiments of the present invention provide a fluid collection container that offers many advantages over prior art designs. A first advantage is that the fluid entry into the container is large and wide. Rather than having a small aperture or specialized receptacle into which liquids are injected from a specialized device, like a syringe, embodiments of the present invention have large surfaces into which liquids may be injected, poured, or otherwise transferred. The large surface requires less accuracy in transferring liquids into the container when compared to prior art designs. Accordingly, a user may transfer fluids into the container more quickly and efficiently without any additional risk of spillage or contamination.

A second advantage is that embodiments of the present invention provide splash-retarding elements that prevent splash back of fluids during transfer to the container. In one or more embodiments, the splash retarding element comprises a cover that is attached to the rim of an opening of a vessel. The splash retarding "cover," in one embodiment, includes a centrally disposed suspended funnel into which fluids are dispensed. A collar is configured to surround the centrally disposed suspended funnel and to "suspend" it within a vessel mounting ring. A plurality of sloping facets circumscribe the collar and slope outwardly from an outer circumference of the collar to the vessel mounting ring. In one embodiment, in the event that the centrally disposed suspended funnel is missed by the health care services provider, the collar and sloping facets work to catch and collect these fluids. The fluids then collect at an intersection nadir defined between the collar and the sloping facts. In one embodiment, a plurality of apertures is disposed along this intersection nadir. The apertures allow the fluids to fall into the collection vessel where they can be absorbed by a coagulant. The incorporation of the splash retarding cover allows a user to transfer fluids into the container more quickly and efficiently without any additional risk of spillage or contamination.

A third advantage is that liquids can be introduced into the container at a wide variety of angles. Prior art containers required users to inject fluids into containers using syringes or other medical devices. The syringes had to be oriented at just the proper angle to engage a specialized receptacle. Alternatively, small openings such as that found in the '314 patent required the user to hold the syringe at a particular angle. With embodiments of the present invention described below, a user may inject, pour, or otherwise transfer fluids into a container at any of a variety of angles without concern of spillage or splash back due to the use of the centrally disposed suspended funnel Moreover, even if the user misses the funnel, the apertures disposed along the intersection nadir of the plurality of facets and collar collects those "errant" fluids and directs them into the fluid collection vessel. Other advantages will be readily apparent to those of ordinary skill in the art having the benefit of this disclosure.

Turning now to FIGS. 1-5, illustrated therein is one embodiment of a splash retarding cover 100 for a fluid containment vessel that is configured in accordance with one or more embodiments of the invention. In one embodiment, the splash retarding cover 100 is manufactured from a clear polypropylene material using a blow molding process along a preform configured to replicate the splash retarding cover 100. Other methods and materials for manufacturing the splash retarding cover 100 will be obvious to those of ordinary skill in the art having the benefit of this disclosure.

The illustrative splash retarding cover 100 of FIGS. 1-5 includes funnel 101 for collecting fluids. The funnel 101 includes a mouth 501 and an exit port 502. In one embodiment, the mouth 501 has a diameter of about fifty-three millimeters. The term "about" is used to denote dimensions that are inclusive of manufacturing and design tolerances. For example, where the manufacturing tolerances are plus or minus 0.5 millimeters, and the design tolerances are plus or minus 1.0 millimeter, "about" fifty-three millimeters could include anything within the range of 51.5 millimeters and 54.5 millimeters.

In one embodiment, the exit port 502 has a diameter of between fourteen and fifteen millimeters. As will be shown below, this diameter is chosen because ten millimeter and twelve millimeter syringes are the most common syringes used in medical procedures. Where convex sidewalls 103 define the boundary of a funnel 101 that begins at a mouth 501 having a diameter of about fifty three millimeters and traverses a funnel height 505 of about forty-one millimeters to an exit port 502 having a diameter of about 14.5 millimeters, a user can place either a ten millimeter or twelve millimeter syringe within the interior of the funnel 101 and have it stand upright without toppling over. This advantageous design allows a user to place a syringe in the funnel 101, discharge its contents, and allow it to drip unattended without worrying about the syringe toppling over and contaminating the area around the fluid containment vessel to which the splash retarding cover 100 is attached. This will be described in further detail with reference to FIG. 20 below.

In this illustrative embodiment, the funnel 101 is centrally disposed along the splash retarding cover 100 to make use of the splash retarding cover 100 more efficient. However, it will be clear to those of ordinary skill in the art having the benefit of this disclosure that the funnel 101 could be non-centrally disposed as well.

In this illustrative embodiment, the funnel 101 is "suspended" in a centrally disposed location along the splash retarding cover 100 by a collar 102. The collar 102 surrounds the funnel 101. In this embodiment the collar 102 and funnel 101 are concentrically arranged relative to each other. While the collar 102 could have flat sides, in this illustrative embodiment the sidewalls 103 of the collar 102 are arched with a convex curvature. In other embodiments, the sidewalls 103 of the collar 102 are arched with a concave curvature.

A plurality of sloping facets 104 circumscribe the collar 102 and slope outwardly and away from an outer circumference 105 of the collar 102. For example, facets 106,107, 108 each extend outward and away from the collar 102 and terminate at a vessel mounting ring 109 that circumscribes the splash retarding cover 100. In this illustrative embodiment, the vessel mounting ring 109, collar 102, and ring formed by the plurality of sloping facets 104 and the funnel 101 are all concentrically aligned.

In one embodiment, the plurality of facets 104 comprise differently shaped facets. For example, in the illustrative embodiment of FIGS. 1-5, the plurality of facets comprises alternating shapes of semi-trapezoidal facets and semi-triangular facets. Facet 106 is a semi-triangular facet, while facet 107 is a semi-trapezoidal facet. The term "semi-" is used because not all edges of each facet are perfectly straight. The edge of facet 106 abutting the vessel mounting ring 109 is curved rather than straight as one illustration.

Figure 2:
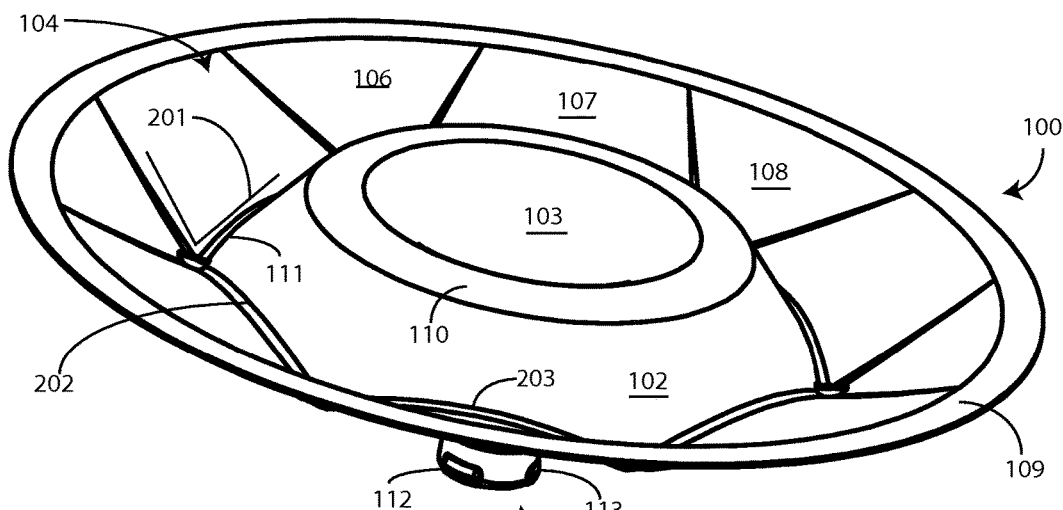
FIG. 2 illustrates another perspective view of one explanatory splash retarding cover for a containment vessel configured in accordance with one or more embodiments of the invention.
Figure 5:
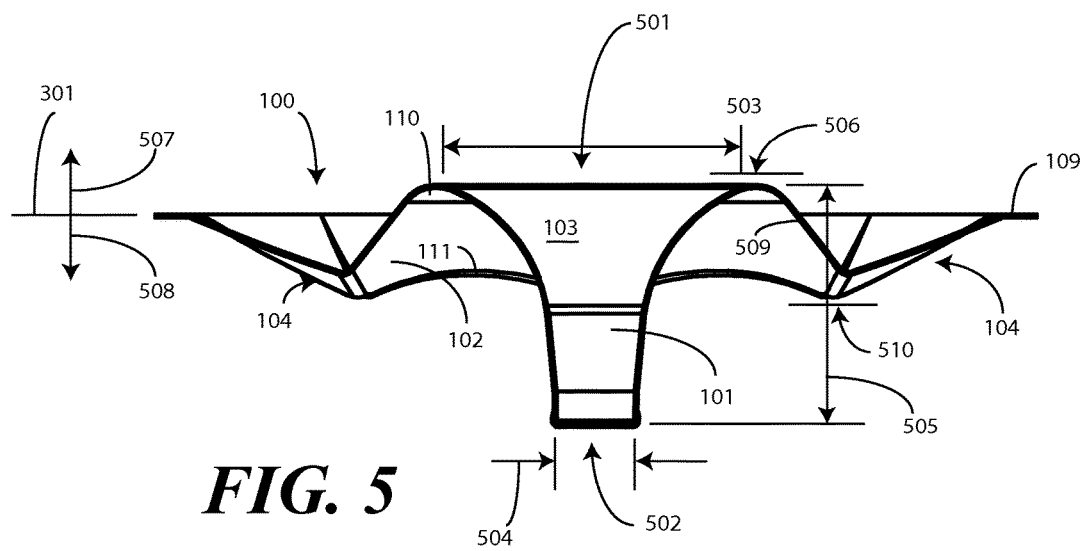
FIG. 5 illustrates a side elevation sectional view of one explanatory splash retarding cover for a containment vessel configured in accordance with one or more embodiments of the invention.

Each of the plurality of facets 104 in this illustrative embodiment slopes outwardly from an outer circumference 105 of the collar 102 and forms a concave angle 201 between the plurality of facets 104 and the collar 102 as shown in FIGS. 2 and 5. Each of the plurality of facets 104 then terminates at the vessel mounting ring 109.

Figure 3:
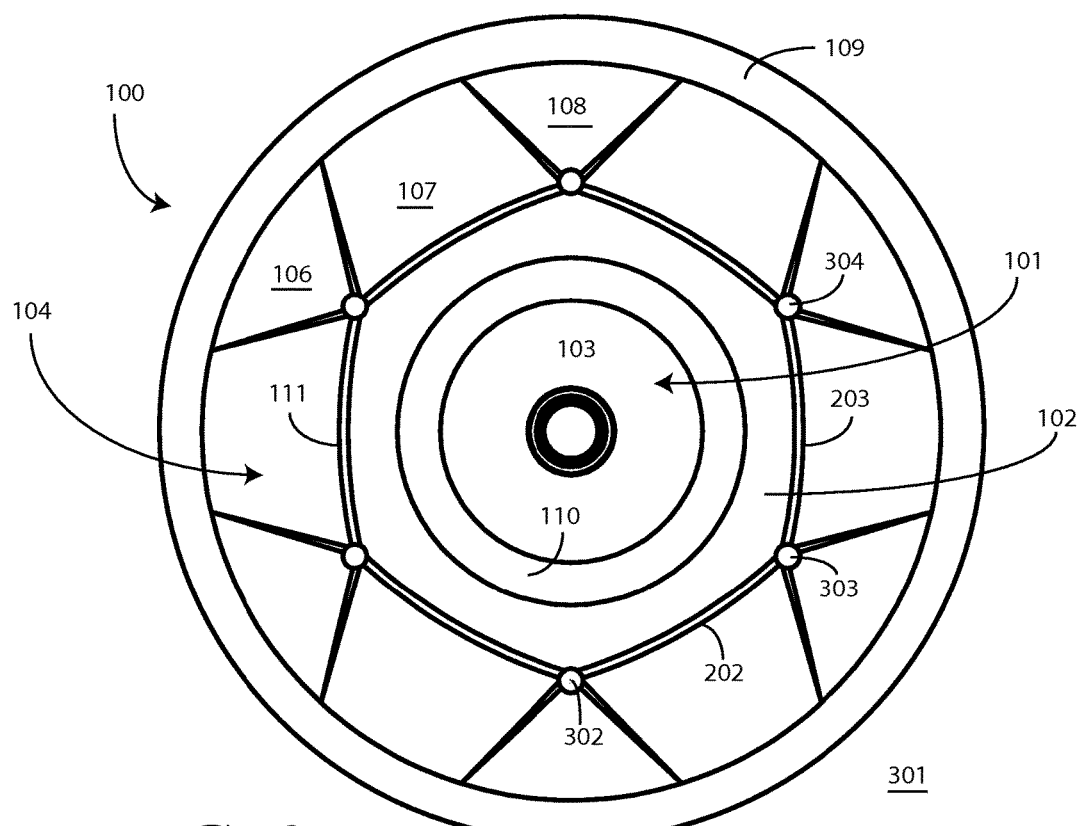
FIG. 3 illustrates a bottom plan view of one explanatory splash retarding cover for a containment vessel configured in accordance with one or more embodiments of the invention.
Figure 4:
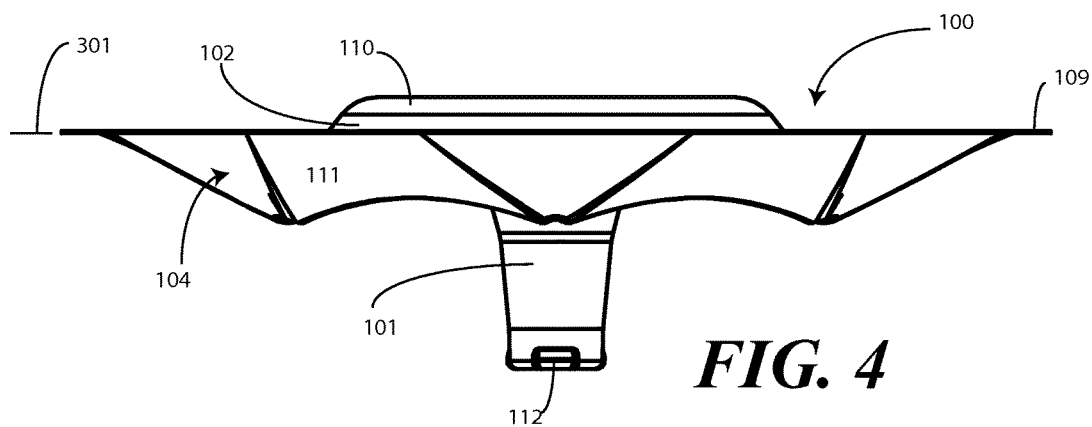
FIG. 4 illustrates a side elevation view of one explanatory splash retarding cover for a containment vessel configured in accordance with one or more embodiments of the invention.

The vessel mounting ring 109 in this illustrative embodiment is an annulus defining a plane 301 parallel to the page of FIG. 3. This plan is also shown in FIGS. 4 and 5. Experimental testing has shown that it can be advantageous to suspend the funnel 101 such that it traverses or transcends the plane 301 defined by the vessel mounting ring 109. For example, as shown in FIG. 5, the funnel 101 runs its height 505 from an apogee 506 disposed at the mouth 501 to the exit port 502. In this configuration, the apogee 506 of the mouth 501 is disposed on a first side 507 of the plane 301 defined by the vessel mounting ring 109 and the exit port 502 is disposed on a second side 508 of the plane 301 defined by the vessel mounting ring 109. In this fashion, the height 505 of the funnel 101 traverses the plane 301 with a portion of the funnel 101 being disposed on the first side 507 and another portion of the funnel 101 being disposed on the second side 508.

In one embodiment, a circumferential ledge 110 is disposed between the funnel 101 and the collar 102. As shown in FIGS. 1-3, in this illustrative embodiment, the circumferential ledge 110 is concentrically disposed between the funnel 101 and the collar 102 at the apogee 506 of the funnel 101 about a perimeter of the mouth 501. In this illustrative embodiment, the circumferential ledge 110 is configured as an annulus. However, those of ordinary skill in the art will appreciate that the circumferential ledge 110 could also be a convex shape that increases the height of the apogee 506 at the crest of the arch defining the convex shape. Concave shapes will generally not be used for fluid collection purposes, but could be used in other applications.

As shown in FIG. 5, the collar 102 extends downward from the apogee 506 of the funnel 101. In this illustrative embodiment, the walls 509 of the collar 102 are generally straight. In other embodiments, the walls 509 could be convex with an arch that extends outward toward the first side 507 of the plane 301 defined by the vessel mounting ring 109. In other embodiments, the walls 509 could be concave with an arch that extends downward toward the second side 508 of the plane 301 defined by the vessel mounting ring 109. FIG. 5 also illustrates how the funnel 101 comprises convex sidewalls 103 that taper from the mouth 501 of the funnel 101 to the exit port 502 of the funnel 101.

In one embodiment, the walls 509 of the collar 102 extend downwardly from the apogee 506 and, where included, the circumferential ledge 110, to intersect the plurality of sloping facets 104 to define an intersection nadir 510 disposed on the second side 508 of the plane 301 defined by the vessel mounting ring 109. Excluding the dimensions of the funnel itself, including the exit port 502, this intersection nadir 510 defines a valley or lowest point of the structure on the second side 508 of the plane 301 defined by the vessel mounting ring 109. As will be described in more detail, one purpose of the intersection nadir 510 is to provide a gravity-fed collection point for any extraneous fluid that escapes the funnel 101 when being delivered to the fluid collection container to which the splash retarding cover 100 is attached. By being disposed lower—relative to the direction in which the earth's gravity pulls objects—than the apogee 506 at the mouth 501 of the funnel 101, extraneous fluids are able to be gravity fed along either the walls 509 of the collar 102 or along the top surfaces of the plurality of sloping facets 104 to the intersection nadir 510 for collection. Since the intersection nadir 510 is disposed beneath the plane 301 defined by the vessel mounting ring 109, these fluids will collect beneath the opening of the fluid collection vessel to which the splash retarding cover 100 is attached. This structure thus helps to protect any spillage of the fluids collected at the intersection nadir 510.

The intersection of the collar 102 and the plurality of sloping facets 104 is referred to as a "segmented ring" 111. The ring is "segmented" because a relatively smooth surface, i.e., the walls 509 of the collar 102, intersects with a more piecewise linear surface, i.e., the plurality of sloping facets 104. Accordingly, this smooth-to-segmented intersection defines the segmented ring 111. As best shown in FIG. 2, in one embodiment the segmented ring 111 defines a plurality of arches, e.g., arches 202,203, which make up the segments of the ring. In this illustrative embodiment, the plurality of sloping facets 104 comprises alternating semi-triangular facets and semi-trapezoidal facets. The arches are defined by the intersection of the semi-trapezoidal facets with the collar 102. Since the semi-triangular facets are disposed point down, each point of each semi-triangular facet intersects a node disposed between the arched segments of the segmented ring 111.

As shown best at FIG. 3, to allow any fluids collected in the intersection nadir 510 to pass into the fluid collection vessel, in one embodiment the segmented ring 111 defines a plurality of apertures, e.g., apertures 302,303,304, at the intersection nadir 510. In this illustrative embodiment, the apertures comprise a plurality of apertures that are concentrically disposed about the funnel 101. Specifically, seven apertures have been included in this explanatory design, with each aperture being separated by an arch that extends from the intersection nadir 510 toward the apogee 506. For example, arch 202 extends from the intersection nadir 510 upward toward the plane 301 defined by the vessel mounting ring 109 and separates apertures 302,303. Similarly, arch 203 separates apertures 303,304. As shown, in this embodiment each aperture is disposed at a point of a corresponding semi-triangular facet. For instance, aperture 303 is disposed at an apex 305 of semi-triangular facet 306.

One other feature of note shown in FIGS. 1, 2, and 4, are mechanical protrusions 112,113. These optional features can be used to selectively couple a cover layer to the splash retarding cover 100 when desired. While configured as protrusions in FIGS. 1, 2, and 4, it will be obvious to those of ordinary skill in the art having the benefit of this disclosure that a recess can be substituted for the protrusions. This will become clearer when considering the cover layer (600) shown in FIG. 6.

Figure 6:
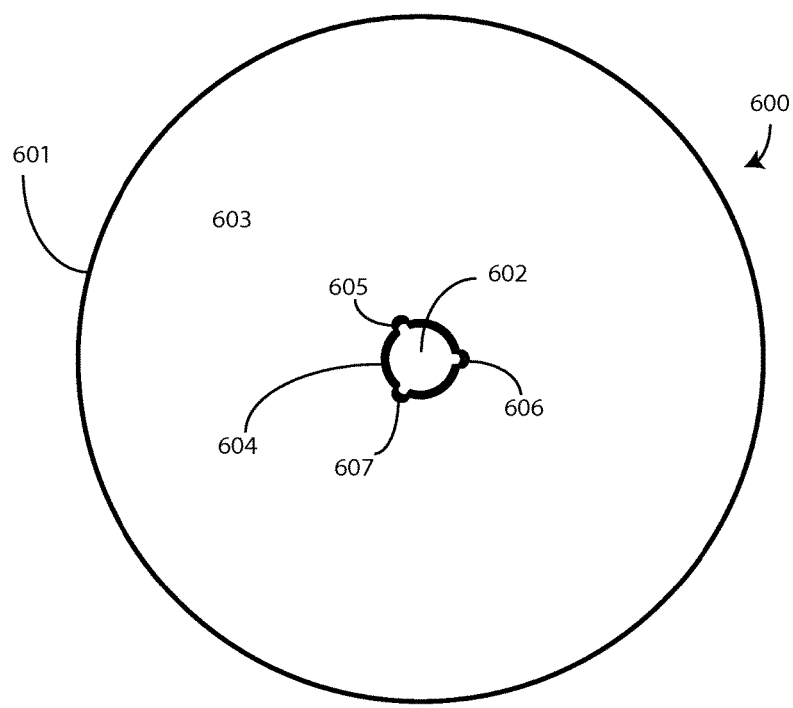
FIG. 6 illustrates a bottom plan view of one embodiment of a cover configured in accordance with one or more embodiments of the invention.

Turning now to FIG. 6, illustrated therein is a bottom plan view of a cover layer 600 configured for use with the splash retarding cover (100) of FIGS. 1-5. The cover layer 600 is configured as a domed surface 603 having an outer perimeter 601 and defining a cover coupling aperture 602 disposed generally at the center of the domed surface 603. The sides 604 of the cover coupling aperture 602 are configured to slide over the mechanical protrusions (112,113) of the funnel (101) of the splash retarding cover (100). Alternatively, the sides 604 of the cover coupling aperture 602 could also be configured to pass into a recess disposed in the sides of the funnel (101) as well.

Disposed about selected portions of the cover coupling aperture 602 are one or more apertures 605,606,607. While three apertures 605,606,607 are shown in FIG. 6, any number of apertures can be used. The apertures 605,606,607 extend away from the funnel (101) when the cover layer 600 is attached to the funnel (101) near the exit port (502) and allow any fluids that pass through the apertures (302,303, 304) disposed along the segmented ring (111) to collect at a base of the cover layer 600 and pass into the fluid collection container disposed beneath the cover layer 600.

Figure 7:
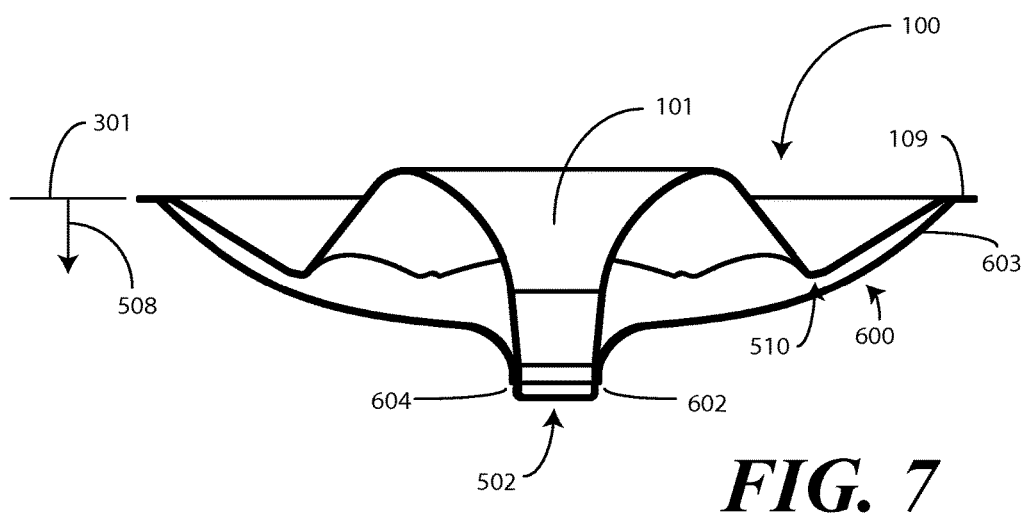
FIG. 7 illustrates a side elevation sectional view of a cover coupled to a splash retarding cover for a containment vessel configured in accordance with one or more embodiments of the invention.
Figure 8:
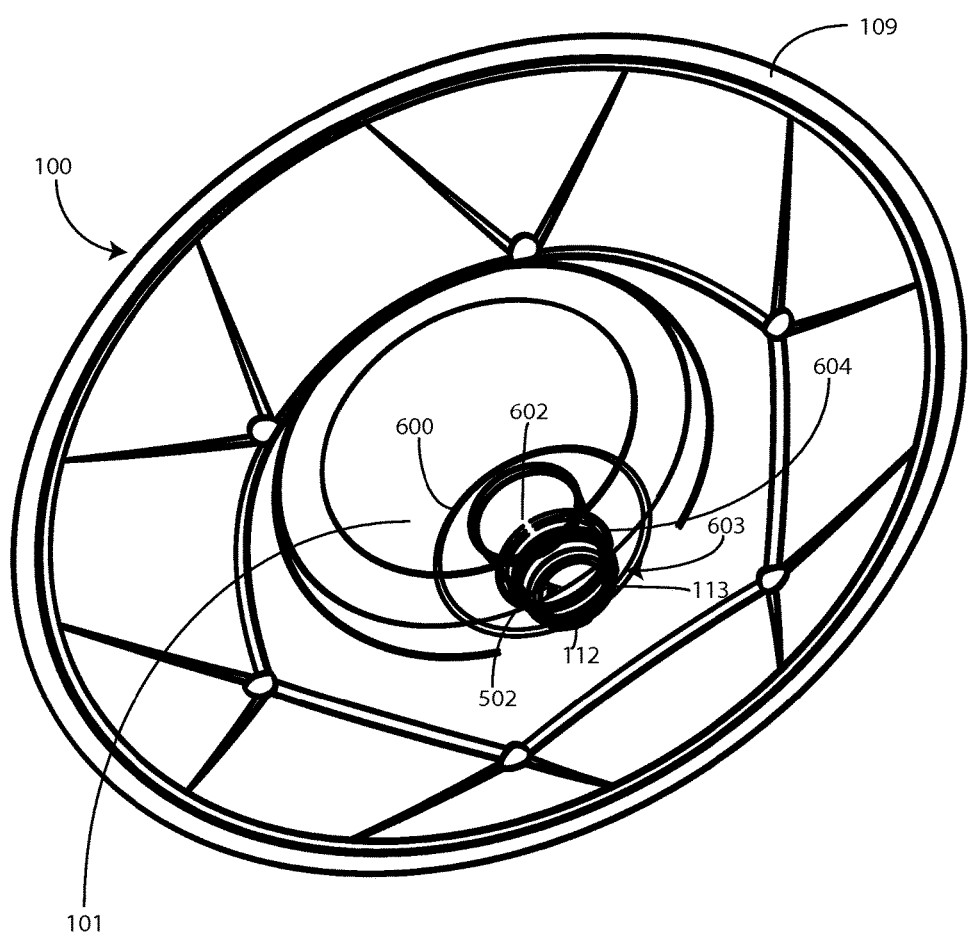
FIG. 8 illustrates a perspective view of a cover coupled to a splash retarding cover for a containment vessel configured in accordance with one or more embodiments of the invention.

Turning now to FIGS. 7 and 8, illustrated therein is the cover layer 600 coupled to the splash retarding cover 100. As shown, the cover coupling aperture 602 passes over the bottom of the funnel 101 substantially at the exit port 502. When this occurs, the sides 604 of the cover coupling aperture 602 pass over the mechanical protrusions 112,113 to "lock" the cover layer 600 onto the funnel 101. Note that where recesses are used instead of the mechanical protrusions 112,113, the sides 604 of the cover coupling aperture 602 can snap into the recesses to lock the cover layer 600 to the funnel 101. In either configuration, the cover layer 600 is therefore mechanically coupled to the funnel 101 on the second side 508 of the plane 301 defined by the vessel mounting ring 109.

As best shown in FIG. 7, the cover layer 600 of this illustrative embodiment extends distally outward and away from the funnel 101 toward the vessel mounting ring 109. The domed surface 603 of the cover layer 600 thus forms a concave surface relative to the funnel 101 on the second side 508 of the plane 301 defined by the vessel mounting ring 109. One reason for this is that it is contemplated that a preventative layer may be preferred to prevent liquids from the fluid collection container, which is disposed on the second side 508 of the plane 301 defined by the vessel mounting ring 109, from being able to exit the fluid collection container through the apertures (302,303,304) disposed at the intersection nadir 510. The cover layer 600 provides this protection while also allowing fluids passing downward (as viewed in FIG. 7) through the apertures(302,303,304) to have a path into the fluid collection container.

This path is defined as follows: when extraneous fluids collect at the intersection nadir 510, they can be gravity fed through the apertures (302,303,304) disposed along the intersection nadir 510. They then drip onto the domed surface 603 of the cover layer 600 where they are drawn by gravity toward the funnel 101. Recall from the discussion of FIG. 6 that one or more apertures (605,606,607) can be disposed substantially at a minimum of the domed surface 603, as is the case in the view of FIG. 7. The fluid can accordingly be gravity fed through the apertures (605,606, 607) disposed about the cover coupling aperture 602 into the fluid collection container. The absence of a direct path out of the fluid collection container through the apertures (302, 303,304) prevents the inadvertent leakage of these fluids that may occur when the fluid collection container was accidentally turned on its side.

Figure 9:
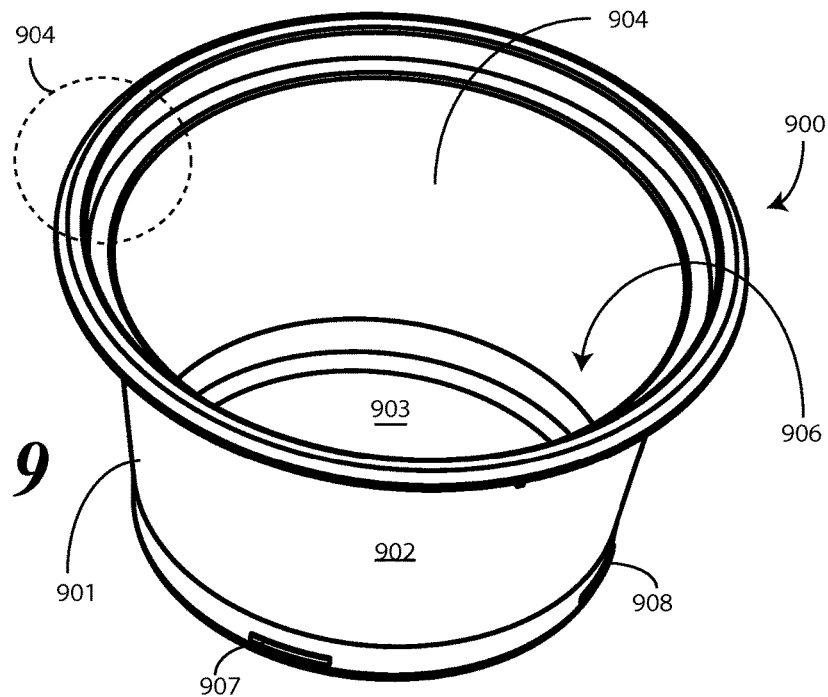
FIG. 9 illustrates a perspective view of one explanatory fluid collection vessel configured in accordance with one or more embodiments of the invention.
Figure 10:
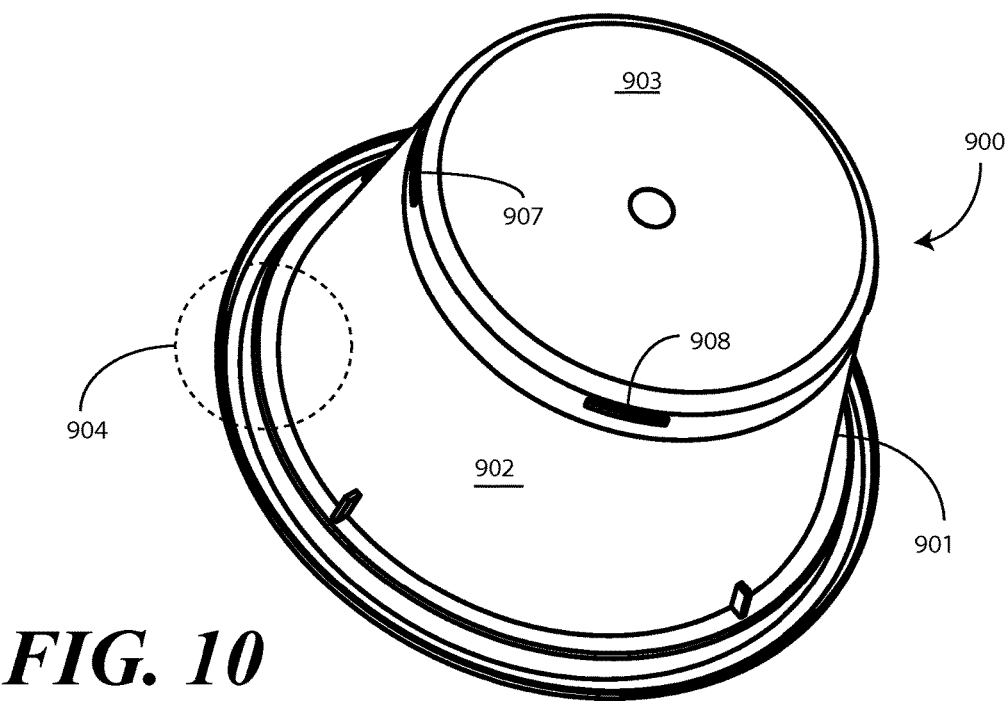
FIG. 10 illustrates another perspective view of one explanatory fluid collection vessel configured in accordance with one or more embodiments of the invention.
Figure 11:
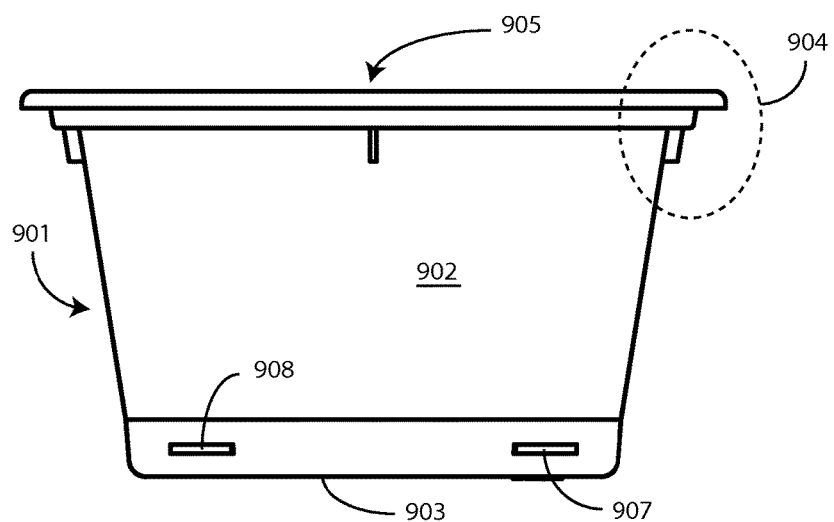
FIG. 11 illustrates a side elevation view of one explanatory fluid collection vessel configured in accordance with one or more embodiments of the invention.
Figure 12:
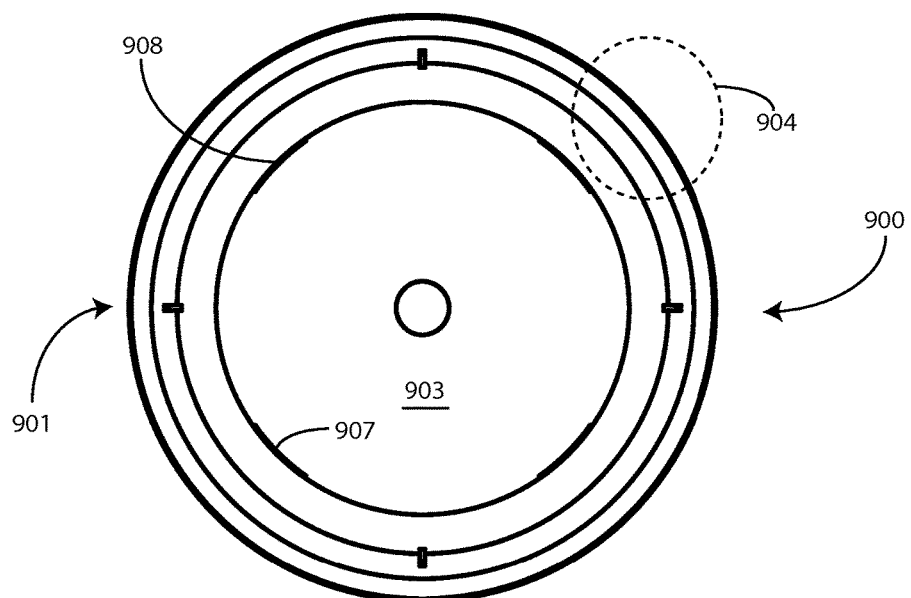
FIG. 12 illustrates a bottom plan view of one explanatory fluid collection vessel configured in accordance with one or more embodiments of the invention.

Turning now to FIGS. 9-12, illustrated therein is one embodiment of a fluid collection container 900 configured for use with the splash retarding cover (100) and cover layer (600) described above. FIGS. 9 and 10 illustrate top and bottom perspective views of the fluid collection container 900, respectively. FIG. 11 illustrates a side elevation view of the fluid collection container 900, while FIG. 12 illustrates a bottom plan view of the fluid collection container 900.

The fluid collection container 900 is configured as a vessel 901. The vessel 901 is defined by a plurality of surfaces having contours configured to form a hollow container, similar to a bowl or cask, which can be used to hold liquid. The vessel 901 can be manufactured in a variety of ways. For example, in one embodiment the vessel 901 can be manufactured from a thermoplastic material such as polypropylene by way of an injection molding process. The vessel 1001 can alternatively be thermally formed on a mold from a soft thermoplastic, such as styrene or polystyrene. In another embodiment, the vessel 901 can be poured on a mold using a quick setting plastic, epoxy, or resin. Other methods of manufacture will be obvious to those of ordinary skill in the art having the benefit of this disclosure.

In one embodiment, the plurality of surfaces defining the vessel 901 includes a bottom surface 903 and a peripheral wall 902. For ease of illustration and efficiency of explanation, the explanatory vessel 901 shown in the figures has a bottom surface 903 that is circular. The bottom surface 903 can be circular or oval, or alternatively can take other rounded shapes. It will be obvious to those of ordinary skill in the art having the benefit of this disclosure that embodiments of the invention are not so limited. The bottom surface 903 could equally be triangular, rectangular, or multisided polygonal as well. Where the bottom surface 903 is polygonal, the corresponding peripheral wall 902 may include facets that intersect at angles corresponding to angles defined by the polygon of the bottom surface 903.

In the illustrative embodiment of FIGS. 9-12, the peripheral wall 902 is round and tapers outward as it extends distally upward from the bottom surface 903. Such a taper can help the vessel 901 be more readily extracted from a manufacturing tool. In this fashion, as shown best in FIG. 10, the bottom surface 903 and the peripheral wall 902 are arranged in a frustoconical geometry. In this embodiment, the peripheral wall 902 terminates in a contoured surface 904. The contoured surface 904 of this illustrative embodiment defines a stair-stepped flanged rim.

The bottom surface 903 and the peripheral wall 902 define an opening 905 disposed at an opposite end of the peripheral wall 902 from the bottom surface 903, and an interior 906 disposed between the opening 905, the bottom surface 903, and the peripheral wall 902. The opening 905 is configured to receive liquids and other substances into the vessel 901. Provided the vessel is in a generally upright position, with the bottom surface 903 disposed below the opening 905 in three-dimensional space, liquids and other substances transferred to the vessel 901 through the opening 905 will be retained in the interior 906 of the vessel 901.

Optional mechanical features 907,908 can be disposed along portions of the peripheral wall 902 so that the vessel 901 can be attached to other objects. For example, the discussion below with respect to FIGS. 13-14, a lid will be disclosed that can cover the opening 905 of the vessel 901. However, in at least one embodiment, the lid can also be coupled to the bottom surface 903 of the vessel 901. In this illustrative embodiment, the mechanical features 907,908 are included to facilitate the coupling of the lid to the bottom portion of the fluid collection container 900.

Figure 13:
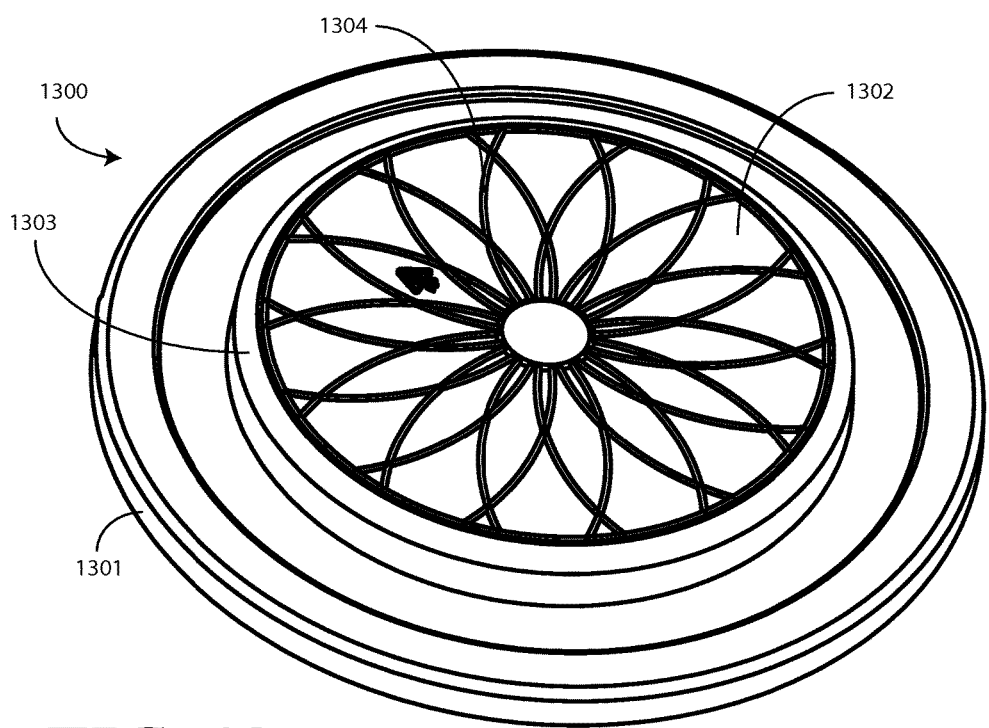
FIG. 13 illustrates a perspective view of one explanatory lid for a fluid collection vessel configured in accordance with one or more embodiments of the invention.
Figure 14:
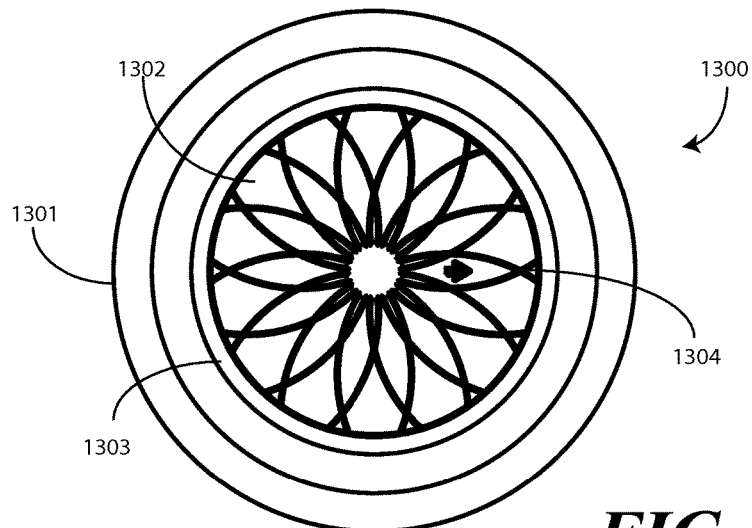
FIG. 14 illustrates a top plan view of one explanatory lid for a fluid collection vessel configured in accordance with one or more embodiments of the invention.

Turning now to FIGS. 13-14, illustrated therein is one explanatory embodiment of a lid 1300 configured in accordance with one or more embodiments of the invention. The lid 1300 is configured for selective attachment to the fluid collection container (900) to form a closed fluid collection container. In one or more embodiments, when the lid 1300 is attached to the vessel (901), a leak-proof seal is formed between vessel (901) and lid 1300.

In one embodiment, so as to be attachable to the vessel (901), the lid 1300 includes an annular wall 1301 disposed about a perimeter of the lid 1300. The annular wall 1301 defines a vessel receiving well disposed beneath a central surface 1302 of the lid 1300 and within the annular wall 1301. The central surface 1302 spans an interior of the lid 1300. In one embodiment, the central surface 1302 is configured with an inclined ring 1303 disposed about the central surface 1302.

In one embodiment, the central surface 1302 comprises a decorative design 1304 that also incorporates functional components. For example, the illustrative lid 1300 of FIGS. 13-14 includes a decorative design 1304 that is a spider pattern. The spider pattern comprises a plurality of ridges that extend distally from the central surface 1302 of the lid 1300. As noted above, in one or more embodiments, the lid 1300 can be coupled to the base of a vessel (901). Where this is the case, the ridges of the spider pattern (or other decorative design 1304) provide frictional components that prevent the lid-vessel assembly from sliding on a work surface. While a spider pattern is one embodiment of a decorative design 1304 that works well in practice to prevent slippage, and that is aesthetically pleasing, it will be clear to those of ordinary skill of the art having the benefit of this disclosure that other decorative designs 1304 could be used as well. For example, in other embodiments the decorative design 1304 could comprise a company logo, product name, or even instructions on how to use the fluid collection container to which the lid 1300 is attached.

Figure 15:
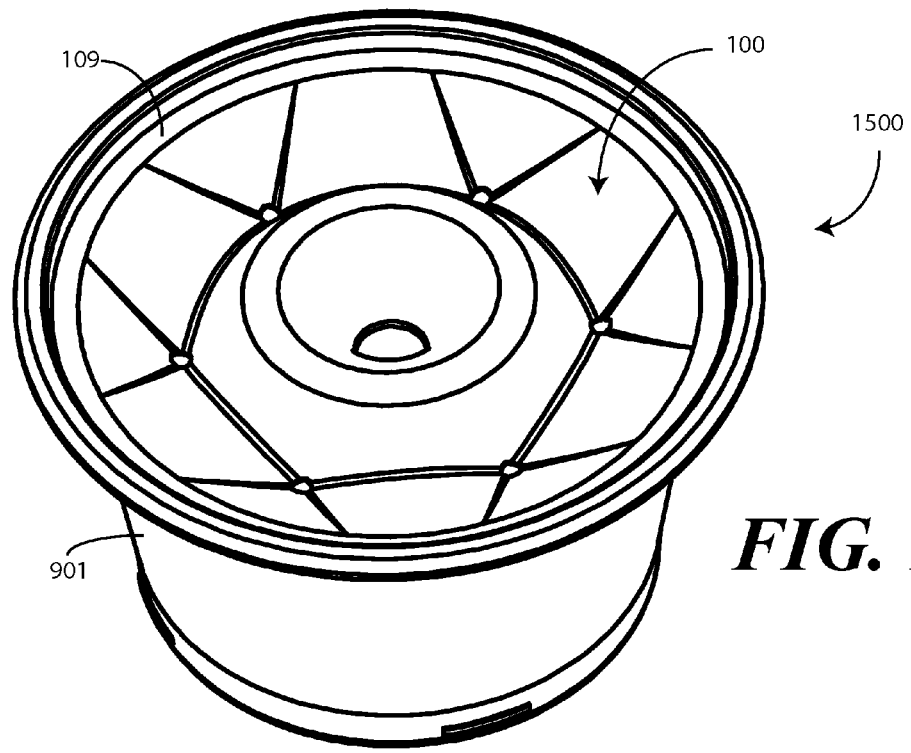
FIG. 15 illustrates a perspective view of one explanatory splash retarding cover coupled to a fluid collection vessel in accordance with one or more embodiments of the invention.
Figure 16:
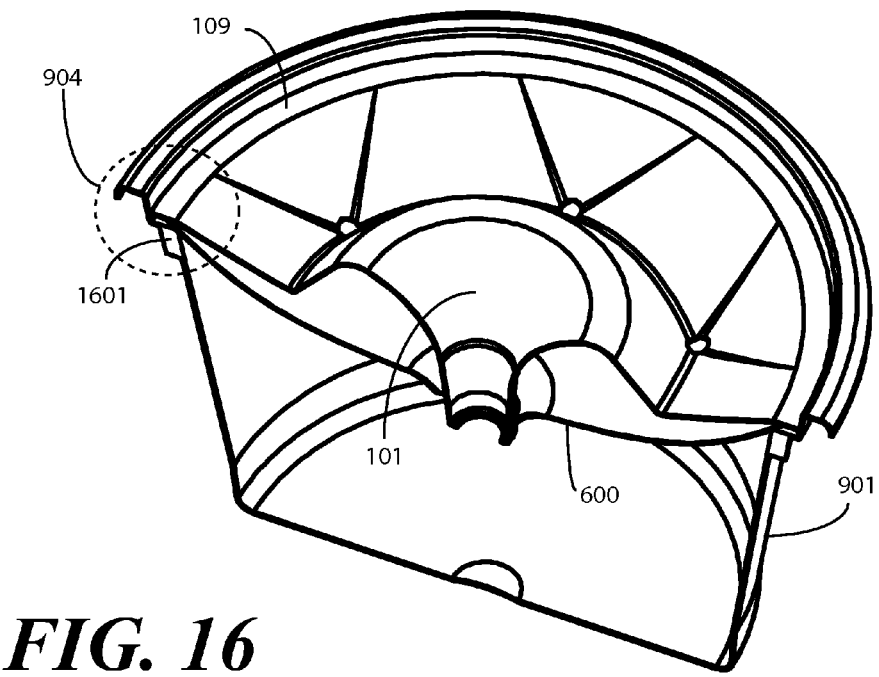
FIG. 16 illustrates a sectional perspective view of one explanatory splash retarding cover coupled to a fluid collection vessel in accordance with one or more embodiments of the invention.

Turning now to FIGS. 15 and 16, illustrated therein is a fluid collection container 1500 configured in accordance with one or more embodiments of the invention. FIG. 15 illustrates a perspective view of the fluid collection container 1500, while FIG. 16 illustrates a sectional view of the fluid collection container 1500. As shown, the fluid collection container 1500 comprises the vessel 901 of FIG. 9 and the splash retarding cover 100 of FIGS. 1-5. The cover layer 600 of FIGS. 6 and 7 has been coupled to the funnel 101 as well.

Recall from above that in one embodiment, the contoured surface 904 of the vessel 901 defined a stair-stepped flanged rim. This stair-stepped flanged rim is shown in the embodiment of FIG. 16. The vessel mounting ring 109 of the splash retarding cover 100 is coupled to a perimeter of the opening (905) of the vessel 901 along a step 1601 of the stair-stepped flanged rim. The coupling could be done by an adhesive, a thermal bonding process, or by other processes. In one embodiment, the coupling between the step 1601 and the vessel mounting ring 109 forms a liquid impermeable seal. Where the vessel 901 included a simple lip or other structure that was different from the stair-stepped flanged rim shown in FIG. 16, the vessel mounting ring 109 would couple to an alternate surface along the perimeter of the opening (905), but the result would be the same—a liquid impermeable seal to prevent liquids from escaping the vessel along the perimeter of the opening (905).

Figure 17:
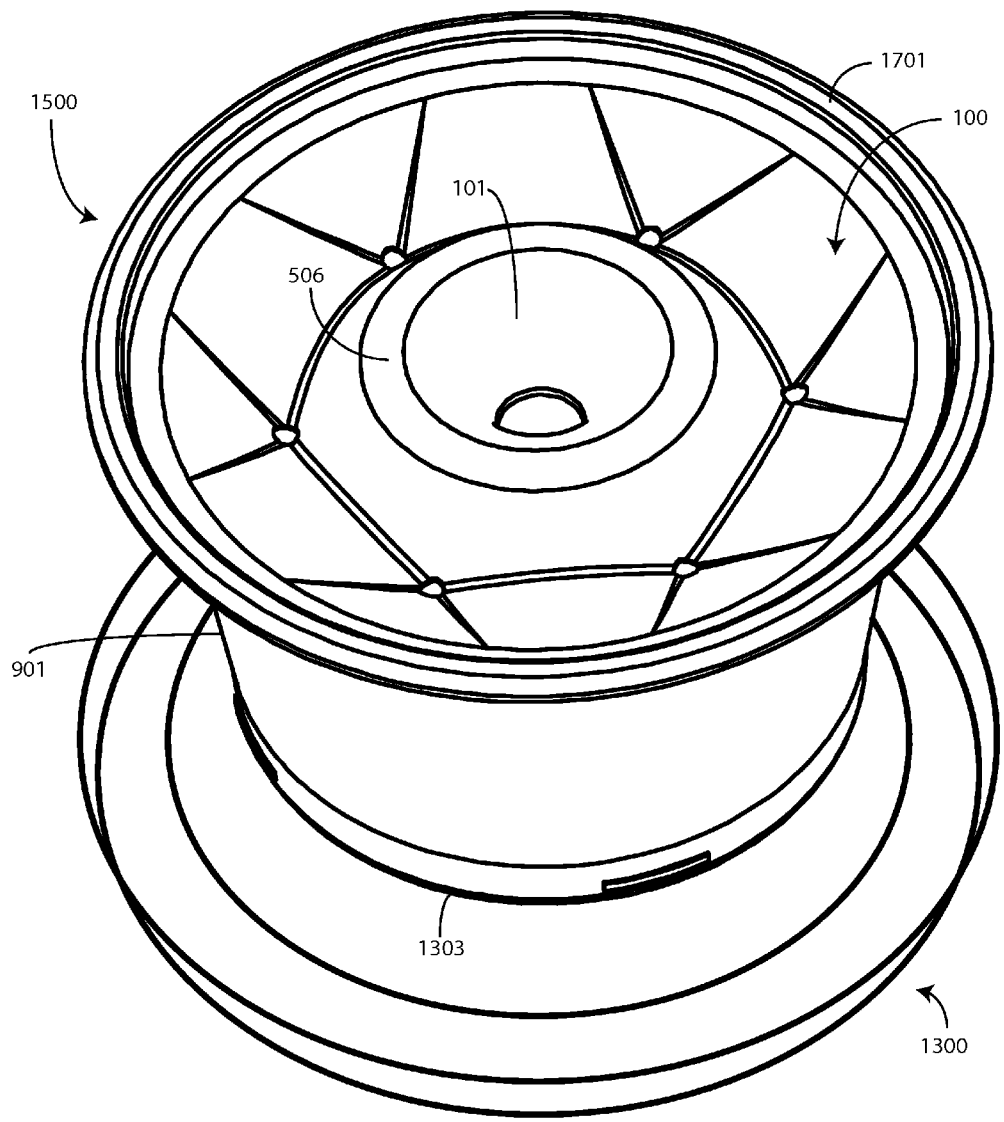
FIG. 17 illustrates a perspective view of one explanatory splash retarding cover coupled to a fluid collection vessel, along with a lid coupled to the base of the fluid collection vessel, in accordance with one or more embodiments of the invention.

Turning now to FIG. 17, illustrated therein is the fluid collection container 1500 of FIGS. 15-16 with the lid 1300 of FIG. 13 disposed beneath the vessel 901. Recall from above that in one embodiment an inclined ring 1303 can be disposed about the central surface (1302) of the lid 1300. In this fashion, the central surface (1302) can be configured to be substantially the same size as the bottom surface (903) of the vessel 901. Accordingly, when the vessel 901 is placed atop the lid 1300 as shown in FIG. 17, the inclined ring 1303 can serve as a retention device that centers the vessel 901 into the lid 1300.

In one embodiment, the vessel mounting ring 109 is configured to seat within the stair-stepped flanged rim by coupling to the step (1601) such that it seats beneath an upper limit 1701 of the vessel 901. When disposed in this position, the apogee 506 of the funnel 101 in the splash retarding cover 100 will not interfere with placement of the lid 1300 atop the vessel 901. When the lid 1300 is placed on the vessel 901 covering the splash retarding cover 100 to create the closed vessel collection container, in one embodiment the apogee 506 touches the interior surface (1302) of the lid 1300. In another embodiment, an air gap is disposed between the lid 1300 and the apogee 506.

Recall from above that in one or more embodiments the lid 1300 can include mechanical features (907) configured to increase friction against a surface when the lid 1300 is inverted and coupled to the bottom surface (903) of the vessel 901 as shown in FIG. 17. The inclusion of the spider pattern of FIGS. 13-14 along the interior surface (1302) of the lid helps to prevent the assembly of FIG. 17 from sliding across a work surface.

In one embodiment, a manufacturer prepares the fluid collection container 1500 and lid 1300 for shipping to customers by pre-attaching the lid 1300 to the bottom surface (903) of the vessel 901. This allows the end user to simply remove the assembly from the packaging for instant use. The user may dispense fluids into the funnel 101. When finished, the user simply detaches the lid 1300 from the bottom surface (903) of the vessel 901 and attaches it to the top of the vessel 901 to form a sealed fluid collection container.

Figure 18:
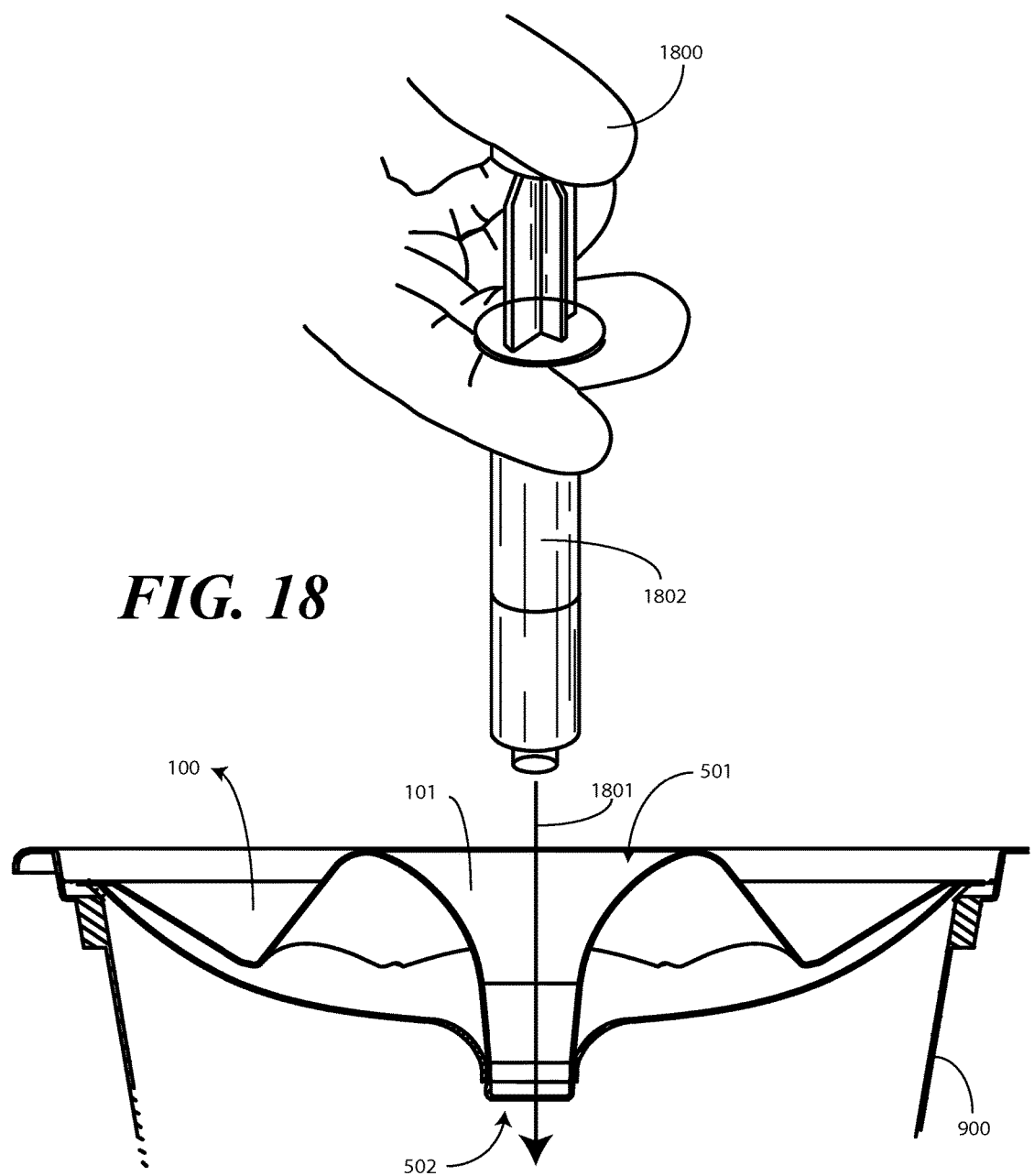
FIG. 18 illustrates a method of using a splash retarding cover in accordance with one or more embodiments of the invention.
Figure 19:
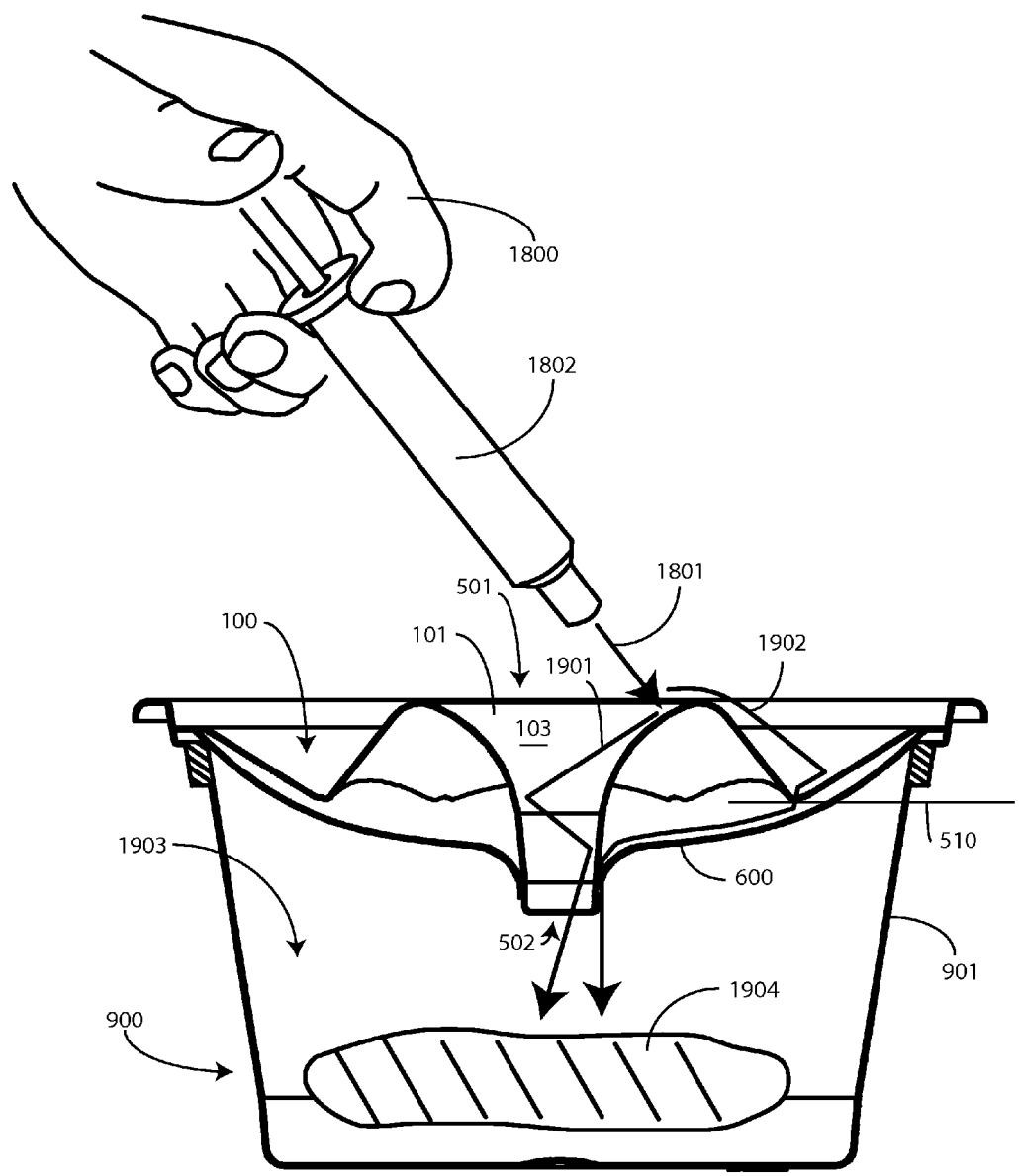
FIG. 19 illustrates another method of using a splash retarding cover in accordance with one or more embodiments of the invention.

Turning to FIGS. 18-19, illustrated therein are some of the many benefits of using a fluid collection container configured in accordance with embodiments of the invention. As shown, a user 1800 is transferring liquid 1801 into the funnel 101 of a splash retarding cover 100 coupled to a fluid collection container 900 by way of a syringe 1802. In FIG. 18, the user 1800 is dispensing the liquid 1801 directly through the funnel 101 by dispensing it into the mouth 501 of the funnel 101 so that it passes straight through to the exit port 502. This is one method of using the fluid collection container.

In FIG. 19, the user 1800 is indirectly dispensing the liquid from the syringe 1802. Specifically, rather than orienting the syringe 1802 orthogonally with the splash retarding cover 100 as was the case in FIG. 18, the syringe 1802 is oriented non-orthogonally relative to the splash retarding cover 100 in FIG. 19. Frequently this latter orientation can be more convenient for the user 1800 based upon the procedure being performed, distance from the fluid collection container, or other external factors. In FIG. 19, some 1901 of the liquid 1801 passes through the funnel 101 by bouncing off the convex sidewalls 103 of the funnel 101. Some other portions 1902 of the liquid 1801 do not accurately enter the mouth 501 of the funnel 101. Accordingly, it falls over the collar 102 to where it collects at the intersection nadir 510. As described above, the other portions 1902 of the liquid 1801 is then able to pass through an aperture (302) disposed at the segmented ring (111) passing about the intersection nadir 510. The other portions 1902 of the liquid 1801 then hits the cover layer 600 and is gravity fed to a minimum of the cover layer 600 located at the exit port 502 of the funnel 101. The other portions 1902 of the liquid 1801 are then passed through the aperture (605) disposed along the sides 604 of the cover coupling aperture 602 into the interior 1903 of the fluid collection container 900.

As illustrated in FIGS. 18-19, with embodiments of the invention, there is no need to engage the syringe 1802 directly into—or in contact with—special connectors or receptacles as was the case with prior art designs. Nor is there any need to hold the syringe 1802 with a particular orientation. To the contrary, the user 1800 may simply hold the syringe 1802 generally above the splash retarding cover 100 and allow the liquid 1801 to flow. The unique contours and surfaces of the splash retarding cover 100 capture the liquid and give it multiple paths through which to pass en route to the interior 1903 of the fluid collection container 900. The cover layer 600 permits gravity fed fluid to pass into the interior 1903 while preventing fluid from escaping from the interior 1903 through any of the apertures (302) disposed along the intersection nadir 510, even when the assembly is turned over on the side.

While the user 1800 is employing a syringe 1802 in this illustrative embodiment, it should be noted that no specialized equipment is required to transfer the liquid 1801 to the fluid collection container. The large surface area of the fluid collecting portions of the splash retarding cover 100 allows fluid from large containers to be simply dumped into the fluid collection container without spillage regardless of whether that liquid is poured into—or around—the funnel 101.

In the illustrative embodiment shown in FIG. 19, the fluid collection container 900 has disposed within its interior 1903 a cache 1904 of coagulant material. The coagulant material is configured to cause liquids to change from a liquid state to a solid or semisolid state. For example, in a medical application the coagulant material can be a blood-specific coagulant configured to transform liquid blood into a gel to prevent spillage. In another embodiment, the coagulant can be a simple coagulant suitable for a variety of liquids. Such coagulants are routinely used as diaper gels in baby diapers. As an alternative to coagulants, in one embodiment the cache 1904 comprises a simple hydrophilic material such as gauze. When the gauze absorbs the inserted liquid, it becomes effectively coagulated by passing into the fibers of the gauze. Other absorbent materials can be substituted for the gauze as well.

Regardless of the material used, the cache 1904 of coagulant material, where included, offers an advantage in that it counterbalances the fluid collection container 900 when it becomes loaded. Said differently, once the cache 1904 gets loaded by fluid absorption, it lowers the center of gravity of the fluid collection container 900, which makes the vessel 901 harder to tip over. In many catheter procedures, a user will simply dump many containers of fluid into the vessel 901. A lower center of gravity allows this to be accomplished more quickly with less spillage.

Figure 20:
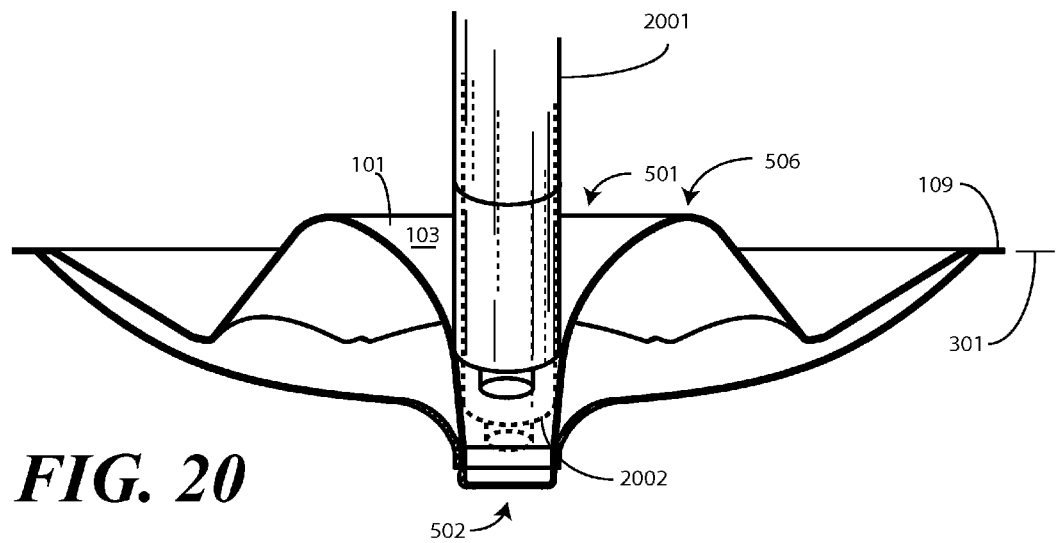
FIG. 20 illustrates a convex tapering wall of a centrally disposed suspended funnel of a splash retarding cover supporting a syringe in an upright position in accordance with one or more embodiments of the invention.

In some applications, the user 1800 will not be able to adequately dispense every last drop of liquid 1801 from the syringe 1802 in a short period of time. The funnel 101 provides a convenient mechanism to allow remaining fluids to drain into the interior 1903 of the fluid collection container 900. Turning now to FIG. 20, one method for facilitating this is shown.

In one or more embodiments, the convex sidewalls 103 of the funnel 101 are configured, when the plane 301 defined by the vessel mounting ring 109 is oriented horizontal to earth with the apogee 506 atop the plane 301, to support either a ten-milliliter syringe 2002 or a twelve-milliliter syringe 2001 inserted into the mouth 501 of the funnel 101 in an upright position. The convex sidewalls 103 do this while preventing either the ten-milliliter syringe 2002 or the twelve-milliliter syringe 2001 from passing through the exit port 502. This is accomplished by providing a convex shape that tapers toward the exit port 502 to a diameter that is less than the width of the smaller of the two syringes, which is the ten-milliliter syringe 2002. As noted above, in one embodiment this diameter is about fourteen millimeters. With the configuration of FIG. 20, the user (1800) can simply place, for example, a twelve-milliliter syringe 2001 into the funnel 101 and leave it there so that any remaining fluids can drain through the exit port 502. This can be done without fear of the twelve-milliliter syringe 2001 toppling over. The same works for the ten-milliliter syringe 2002. This is a significant advantage when compared to prior art designs, as none of the prior art designs are capable of supporting multiple sized syringes in a generally upright position.

Figure 21:
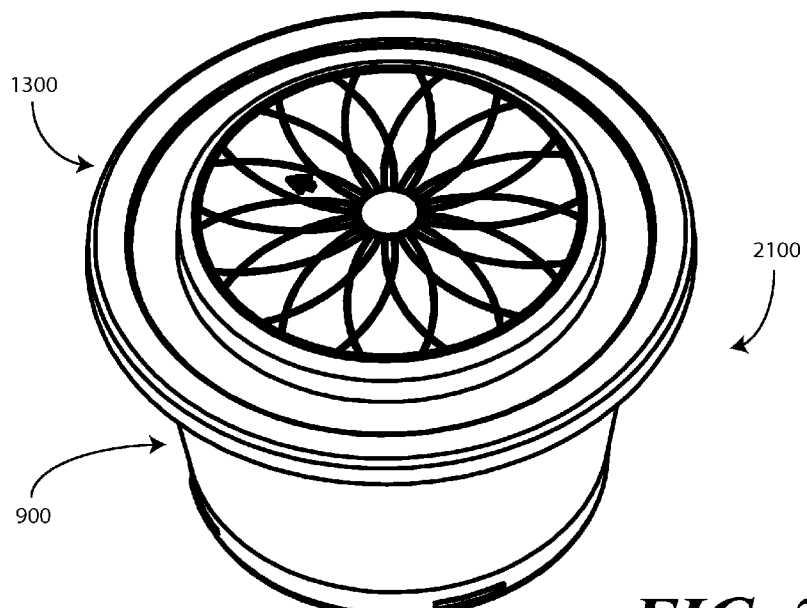
FIG. 21 illustrates perspective view of a closed fluid collection container configured in accordance with one or more embodiments of the invention.
Figure 22:
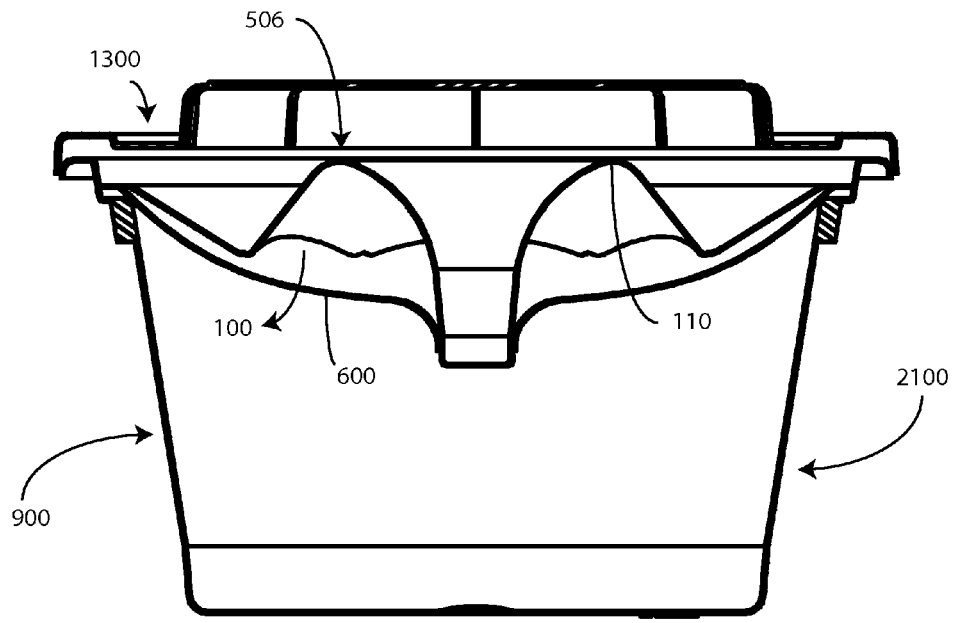
FIG. 22 illustrates a sectional view of a closed fluid collection container configured in accordance with one or more embodiments of the invention.
Figure 23:
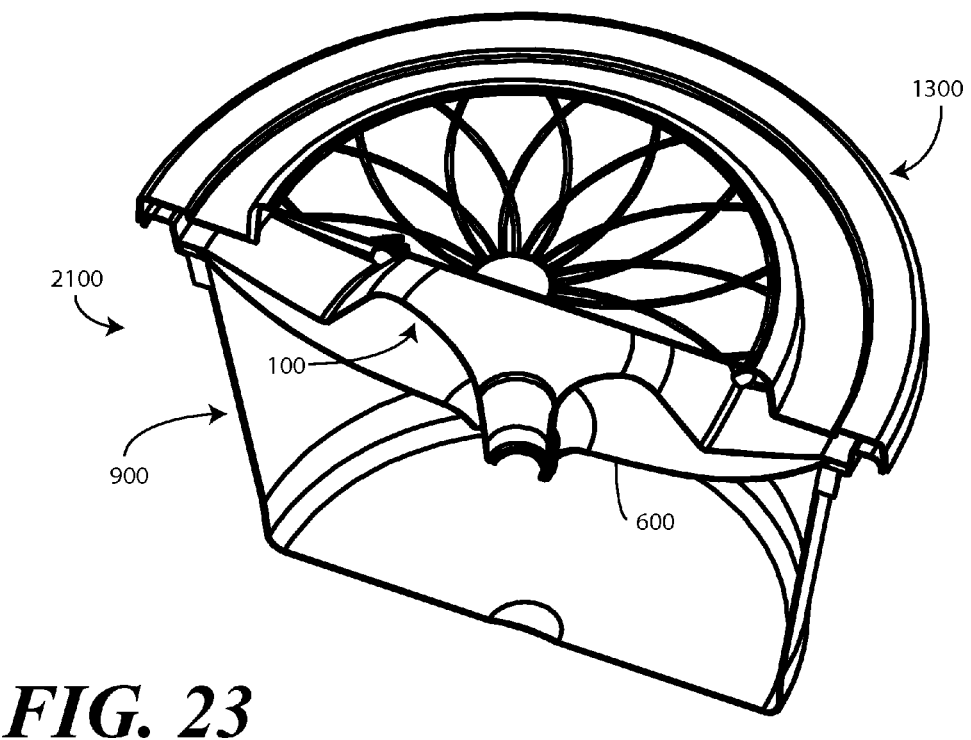
FIG. 23 illustrates another sectional view of a closed fluid collection container configured in accordance with one or more embodiments of the invention.

Once the user (1800) is done dispensing fluids into the funnel 101, or allowing them to drain into the same by leaving the syringe disposed in the funnel 101 in the upright position, the user is ready to seal the fluid collection container with the lid. Turning now to FIGS. 21-23, illustrated therein is a sealed fluid collection container 2100 with the lid 1300 securely sealed atop the fluid collection container 900. As shown best in FIG. 22, in this illustrative embodiment the apogee 506 defined by the circumferential ledge 110 abuts the bottom of the lid 1300 when the lid 1300 is attached to the fluid collection container 900. The lid 1300 completely covers the splash retarding cover 100 and cover layer 600, thereby completely preventing any spillage or leakage from the sealed fluid collection container 2100.

Figure 24:
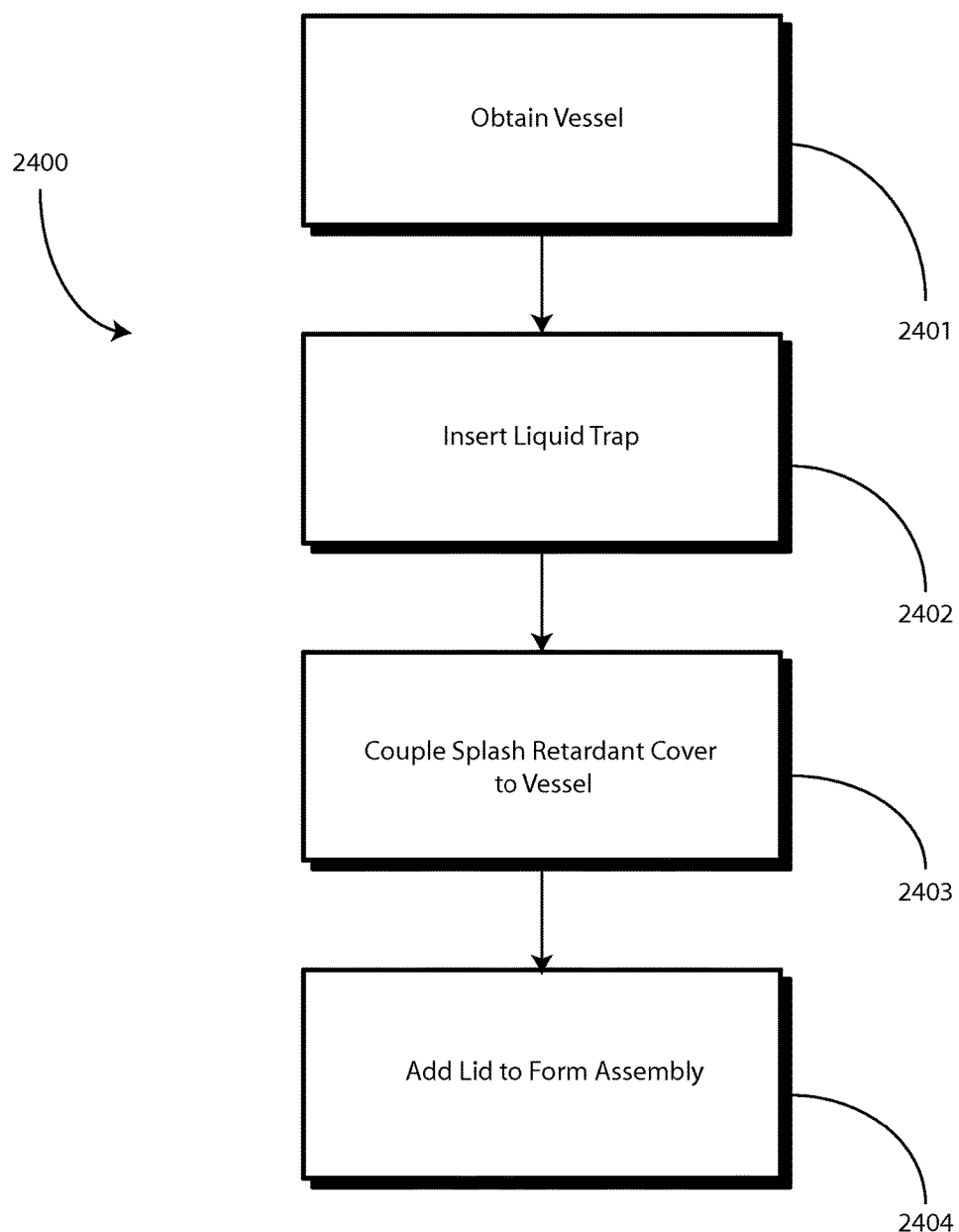
FIG. 24 illustrates one method of manufacturing a fluid collection container configured in accordance with one or more embodiments of the invention.

Turning to FIG. 24, illustrated therein is one method 2400 of manufacturing a fluid collection container in accordance with one or more embodiments of the invention. The process steps have largely been described in conjunction with the apparatus drawings above, and so will only be cursorily discussed here.

At step 2401, a manufacturer obtains a fluid collection vessel. As noted above, this can be manufactured from an injection molding process, procured from a third-party vendor, or manufactured by other methods. At step 2402, the manufacturer optionally inserts a liquid trap into the interior of the vessel. In one embodiment, the liquid trap is a cache of coagulant, such as a gelling agent or an absorbent material.

At step 2403, the manufacturer couples a splash retarding cover to a vessel. In one embodiment, the splash retarding cover comprises a centrally disposed suspended funnel, a collar surrounding the centrally disposed suspended funnel, a vessel mounting ring, and a plurality of sloping facets circumscribing the collar and sloping outwardly from an outer circumference of the collar and terminating at the vessel mounting ring.

At step 2404, the manufacturer attaches a lid to the vessel. In one embodiment, the lid is configured to attach to the vessel either at the base of the vessel or over the splash retarding cover to form a closed fluid collection container. Where this is the case, in one embodiment step 2404 comprises attaching the lid to the base of the vessel to make the initial use easier for the end user by obviating the need for a user to first remove the lid and then attach it to the bottom of the vessel. The lid can be packaged with the assembled vessel to form a fluid collection container ready for shipment to a user.

Figure 25:
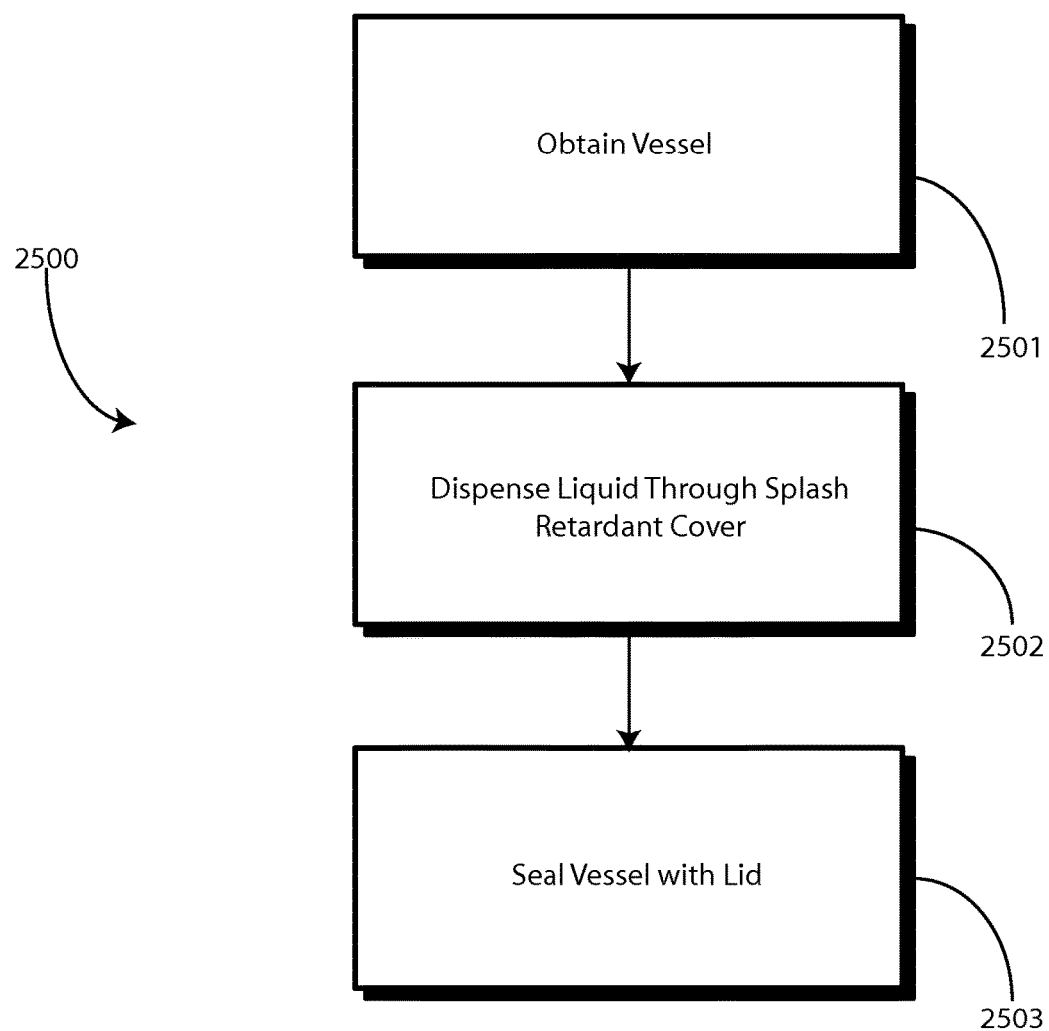
FIG. 25 illustrates a method of using a fluid collection container configured in accordance with one or more embodiments of the invention.

The user is then able to use the fluid collection container in accordance with the method 2500 shown in FIG. 25. At step 2501, the fluid collection container is obtained from the manufacturer. At step 2502, the user transfers a liquid substance to the fluid collection container by passing the liquid substance through the splash retarding cover disposed across an opening of the fluid collection container. In one embodiment, this step 2502 comprises transferring a liquid substance to the fluid collection container by passing the liquid substance through a splash retarding cover comprising a centrally disposed suspended funnel, a collar surrounding the centrally disposed suspended funnel, and a plurality of sloping facets circumscribing the collar and sloping outwardly from an outer circumference of the collar to a perimeter of an opening of the vessel. At step 2503, the user optionally attaches a lid to the fluid collection container to form a sealed fluid collection container.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A splash retarding cover for a containment vessel, the splash retarding cover comprising:
   a centrally disposed suspended funnel;
   a collar surrounding the centrally disposed suspended funnel;
   a vessel mounting ring; and
   a plurality of sloping facets circumscribing the collar and sloping outwardly from an outer circumference of the collar and terminating at the vessel mounting ring;
   wherein:
      the centrally disposed suspended funnel comprises a mouth and an exit port;
      the collar is configured to suspend the centrally disposed suspended funnel such that an apogee of the mouth is disposed on a first side of a plane defined by the vessel mounting ring and the exit port is disposed on a second side of the plane defined by the vessel mounting ring.

2. The splash retarding cover of claim 1, further comprising a circumferential ledge disposed concentrically between the centrally disposed suspended funnel and the collar at the apogee.

3. The splash retarding cover of claim 1, wherein the collar intersects the plurality of sloping facets at a segmented ring defining an intersection nadir disposed on the second side of the plane defined by the vessel mounting ring.

4. The splash retarding cover of claim 3, wherein the segmented ring defines on or more apertures disposed along the intersection nadir.

5. The splash retarding cover of claim 4, wherein the one or more apertures comprise a plurality of apertures that are concentrically disposed about the centrally disposed suspended funnel.

6. The splash retarding cover of claim 5, wherein each aperture of the plurality of apertures is separated from another aperture by an arch extending from the intersection nadir toward the apogee.

7. The splash retarding cover of claim 3, wherein the plurality of sloping facets comprises alternating semi-trapezoidal facets and semi-triangular facets.

8. The splash retarding cover of claim 7, wherein each of the one or more apertures are disposed at a point of corresponding semi-triangular facet.

9. The splash retarding cover of claim 1, wherein the centrally disposed suspended funnel comprises convex sidewalls that taper from the mouth of the centrally disposed suspended funnel to the exit port of the centrally disposed suspended funnel.

10. The splash retarding cover of claim 9, wherein the convex sidewalls are configured, when the plane defined by the vessel mounting ring is oriented horizontal to earth with the apogee atop the plane, to support one of a ten-milliliter syringe or a twelve-milliliter syringe inserted into the mouth in an upright position while preventing the one of the ten-milliliter syringe or the twelve-milliliter syringe from passing through the exit port.

11. The splash retarding cover of claim 1, further comprising a cover layer configured to mechanically couple to the centrally disposed suspended funnel on the second side of the plane defined by the vessel mounting ring and to extend toward the vessel mounting ring, thereby defining a concave surface relative to the centrally disposed suspended funnel on the second side of the plane defined by the vessel mounting ring.

12. The splash retarding cover of claim 11, wherein the cover layer defines one or more apertures disposed substantially at a minimum of the concave surface.

13. The splash retarding cover of claim 1, further comprising a vessel having an opening, wherein the vessel mounting ring is coupled to a perimeter of the opening.

14. The splash retarding cover of claim 13, further comprising a lid configured to attach to the vessel over the splash retarding cover to form a closed fluid collection container.

15. The splash retarding cover of claim 14, wherein the lid is configured to be attachable to a base of the vessel, further wherein the lid comprises mechanical features configured to increase friction against a surface when inverted and coupled to the base of the vessel.

16. The splash retarding cover of claim 14, further comprising a cache of coagulant disposed within an interior of the vessel.

17. A method of manufacturing a fluid collection assembly, comprising:

coupling a splash retarding cover to a vessel the splash retarding cover comprising:

a centrally disposed suspended funnel;

a vessel mounting ring;

a collar surrounding the centrally disposed suspended funnel the collar to suspend the centrally disposed suspended funnel such that an apogee of a mouth of the funnel is disposed on a first side of a plane defined by the vessel mounting ring and an exit port is disposed on a second side of the plane defined by the vessel mounting ring; and a plurality of sloping facets circumscribing the collar and sloping outwardly from an outer circumference of the collar and terminating at the vessel mounting ring; and attaching a lid to a base of the vessel, the lid being configured to attach to the vessel either at the base of the vessel or over the splash retarding cover to form a closed fluid collection container.

* * * * *